(12) United States Patent
Senge

(10) Patent No.: US 7,131,438 B2
(45) Date of Patent: Nov. 7, 2006

(54) HERBAL STEAM DEVICE

(75) Inventor: Wolfgang Senge, Sandersdorf (DE)

(73) Assignee: Ionto-Comed GmbH, Eggenstein-Leopoldshafen (DE)

(*) Notice: Subject to any disclaimer, the term of this patent is extended or adjusted under 35 U.S.C. 154(b) by 9 days.

(21) Appl. No.: 10/809,973

(22) Filed: Mar. 25, 2004

(65) Prior Publication Data
US 2004/0187797 A1     Sep. 30, 2004

(30) Foreign Application Priority Data
Mar. 26, 2003 (DE) ............................ 103 13 666
Jul. 8, 2003  (DE) ............................ 103 30 681

(51) Int. Cl.
   F24F 6/18   (2006.01)
   B05B 1/24   (2006.01)
(52) U.S. Cl. .................... 126/389.1; 239/136; 604/291
(58) Field of Classification Search ............ 126/389.1, 126/373.1, 350.2; 604/289, 291; 4/537; 392/403, 394; 239/139, 136; 122/508
See application file for complete search history.

(56) References Cited
U.S. PATENT DOCUMENTS

| | | | | |
|---|---|---|---|---|
| 2,200,008 | A | * | 5/1940 | Nowak ............... 4/535 |
| 2,526,027 | A | * | 10/1950 | Huck ............... 126/389.1 |
| 4,300,556 | A | * | 11/1981 | Ochi et al. ............... 604/291 |
| 5,098,414 | A | * | 3/1992 | Walker ............... 604/291 |
| 5,423,485 | A | | 6/1995 | Tagusari |
| 5,607,409 | A | * | 3/1997 | John ............... 604/289 |
| 6,236,808 | B1 | | 5/2001 | Jordan et al. |
| 6,282,369 | B1 | | 8/2001 | Maier et al. |
| 6,712,290 | B1 | * | 3/2004 | Chien ............... 239/136 |

FOREIGN PATENT DOCUMENTS

| | | |
|---|---|---|
| DE | 41 09 357 A1 | 9/1992 |
| FR | 1 500 935 | 1/1968 |
| FR | 2 460 644 A * | 3/1981 |
| GB | 2 253 786 A | 9/1992 |
| WO | WO 2004/018936 A1 | 3/2004 |

OTHER PUBLICATIONS

Assembly Instructions, Ionto-Herb, 1 page, Sep. 2001.
Operating Instructions, Ionto-Herb, 3 pages, Aug. 2002.
Operating Instructions, Ionto-Herb® Oxy, Ionto-Herb® Oxy Peel, Ionto-Herb® XL, 5 pages, Jan. 2002.

* cited by examiner

Primary Examiner—Josiah C. Cocks
(74) Attorney, Agent, or Firm—Brinks Hofer Gilson & Lione

(57) ABSTRACT

A herbal steam device includes a closed heated boiling chamber with openings at the side for a steam outlet. A collecting chamber surrounds the upper part of the boiling chamber. Cold water from a reservoir below flows into the boiling chamber through an inflow pipe. Surplus water flows through an overflow and a backflow pipe back to the reservoir. An electrical heating plate is present under the boiling chamber, and a herb pot may be placed in the steam space above the boiling chamber. The inflow pipe runs in a curve around the boiling chamber. The steam which escapes from the openings heats up the inflowing water. At the same time, the relatively cold inflow pipe acts as a foam barrier adjacent to the openings.

24 Claims, 6 Drawing Sheets

HERBAL STEAM DEVICE

CROSS REFERENCE TO RELATED APPLICATIONS

This application claims priority to German patent application DE 103 13 666.5, filed Mar. 26, 2003 and DE 103 30 681.1, filed Jul. 8, 2003.

BACKGROUND

1. Technical Field

This invention relates to a herbal steam treatment device that may create steam enriched with essential oils of herbs or plant extracts.

2. Background Information

Herbal steam, which is also called flavour steam, has a very positive effect on the skin. On the one hand it stimulates the metabolism and on the other hand it is relaxing and comforting. The skin becomes softer and more elastic; blood circulation and metabolism are stimulated. Thereby the receptiveness of the skin increases for the effects of the corresponding plant extracts or essential oils.

The herbal steam device "IONTO-HERB" available from IONTO-COMED of Eggenstein-Leopoldshafen, Germany, includes a steam pot of high-grade steel with an integrated heating plate. A removable lid provides access to fill the steam pot. However, the entire quantity of water in the steam pot must be heated up whenever the steam device is used. In the steam space a herb sieve is arranged. The steam, enriched with essential oils, is led through a steam pipe to a steam outlet. By the direct arrangement of the herb sieve above the steam pot it is inevitable that condensed water which is enriched with oil flows back to the steam pot. The foam that arises can be accepted to a certain degree. If, however, the foam reaches a certain height, the heating must be switched off immediately to prevent ebullient foam. Otherwise the foam may reach the steam outlet over the steam tube and hot water droplets from the bursting bubbles could reach the person to be treated. This undesirable effect is sometimes referred to as the "Spittle" of the steam device.

The herbal steam device "IONTO-HERB XL," also from IONTO-COMED, includes a steam pot which is filled with water over a filler neck with an unscrewable clasp until full. The water in the steam pot boils with the help of the electrical heater. The arising steam passes through a horizontal steam channel into a herb stub, thereby enriching the steam with essential oils. The enriched steam then passes further through the outlet of a steam pipe. The condensate arising in the steam pipe flows through a condensate outlet and is collected in a condensate beaker separated from the steam pot. Therefore, the condensate with the essential oils does not get into the steam pot. When used correctly no foam can arise so that, as a rule, there is no danger of ebullient foam or even "Spittle." However, the condensate beaker must be drained frequently in order to prevent it from overflowing. The electrical heater of the steam pot is switched off automatically when the condensate state reaches its maximum state. One disadvantage of this device is that its wide construction requires a correspondingly stable stand with heavy base plate.

Both described herbal steam devices have a long heating-up time because after filling, the entire volume of water must be heated until it boils. In addition, through costly control electronics with liquid level sensors, it must be ensured that the heater is only switched on when the operating conditions are perfect.

Therefore, a need has long existed for an improved herbal steam device that may have a simple and space-saving construction, short heating-up time, long uninterrupted treatment period, ease of use, and high operational safety.

BRIEF SUMMARY

In one implementation, a herbal steam device includes a boiling chamber, a collecting chamber and a reservoir that may hold cold fresh water and may be separated from the collecting chamber. The boiling chamber may be relatively small so that a relatively small quantity of water is boiled and the heating-up time is shorter. However, at the same time the possible duration of uninterrupted application of the steam treatment is extended considerably according to the capacity of the reservoir. Due to the small water volume in the boiling chamber and the possibility to supply continually fresh water from the reservoir, the tendency to foam is low. Ebullient foam is essentially eliminated.

The reservoir for cold water may be placed under the boiling chamber and the collecting chamber which communicates with the boiling chamber. The cold water may be pumped effectively by an electrically driven pump in the inflow pipe from the reservoir to the boiling chamber. By an overflow in the reservoir which flows into a backflow pipe, surplus condensate and/or condensate in the steam space may flow back into the reservoir. As a result, the water level in the boiling chamber automatically remains approximately constant, although cold fresh water may flow continuously into the boiling chamber. The device effectively prevents condensate enriched with essential oils from entering the boiling chamber, further reducing the potential for foaming.

The backflow pipe may end in the bottom area of the reservoir below the water line. As the other end of the backflow pipe is in connection with the steam space over the overflow, there is a pressure balance between the steam pressure in the steam space and the counterpressure in the lower section of the backflow pipe which is made up of air pressure and water pressure. This pressure balance may function as a pressure relief valve. If the steam way or even the outlet should be blocked, the overpressure in the steam space can escape through the backflow pipe into the reservoir which has a relatively large volume. The liquid level height of the water in the reservoir thereby limits the maximum pressure in the steam space.

In one implementation, the boiling chamber is closed at the top, and the boiling chamber has openings at the side for a steam outlet. The collecting chamber may abut on the boiling chamber and the steam space may be formed over the boiling chamber and the collecting chamber. Condensate appearing in the steam space is kept away from the boiling chamber and drops automatically into the collecting chamber where it is drained off together with the surplus water to the reservoir. A higher concentration of the condensate with essential oils and/or plant extract in the boiling chamber is thereby effectively prevented. However, at the same time the steam outlet is not hindered by the openings at the side of the boiling chamber.

The boiling chamber may be cylindrical, and the openings for steam outlet may lie in a narrow band in the upper section of the side wall of the boiling chamber. The collecting chamber which may also be cylindrical and may concentrically surround an upper section of the steam chamber. The result is a narrow construction form for the steam treatment device.

In one implementation, the inflow pipe is led through the steam space near the openings of the boiling chamber. If the boiling chamber is cylindrical, the inflow pipe may pass in a curve around the boiling chamber. Accordingly, on the one hand the water pumped up from the reservoir is pre-heated so that the difference in temperature is reduced when flowing in into the boiling chamber. This saves heating energy and leads to thermic stability. On the other hand, bubbles which come through the openings at the side of the boiling chamber immediately hit and burst on the cooled inflow pipe. The inflow pipe around the boiling chamber beside the openings therefore forms a foam barrier.

For a cylindrical and concentric configuration of the boiling chamber, collecting chamber, and steam space the steam treatment device may close the steam space from above by a removable, pressure-sealed lockable lid. Additionally, the steam treatment device may include a herbal stub under the lid in which a herbal pot is set. When taking off the lid the device may be easily filled with fresh water from above; the water then runs through the herbal stub downwards first into the collecting chamber and then through the overflow, through the connected backflow pipe, and to the reservoir. After filling, the herbal pot may be set in the herbal stub and lid may then be secured. The steam treatment device is ready for operation until the reservoir is empty or the herbs in the herb pot should be replaced.

BRIEF DESCRIPTION OF THE DRAWINGS

FIG. 1b shows a top view of the herbal steam treatment device shown in FIG. 1a.

FIG. 2b illustrates a top view of the herbal steam treatment device of FIG. 2a.

FIG. 3a shows a vertical section of an upper part of the herbal steam treatment device shown in FIG. 2a.

FIG. 3b shows a horizontal section of the upper part of the herbal steam treatment device shown in FIG. 3a.

FIG. 4a shows a second vertical section of the upper part of the herbal steam treatment device shown in FIG. 2a.

FIG. 4b shows a second horizontal section of the upper part of the herbal steam treatment device shown in FIG. 4a.

FIG. 5 illustrates a perspective partial view of the upper part of the herbal steam treatment device shown in FIG. 2a.

DETAILED DESCRIPTION

Figure 1A:
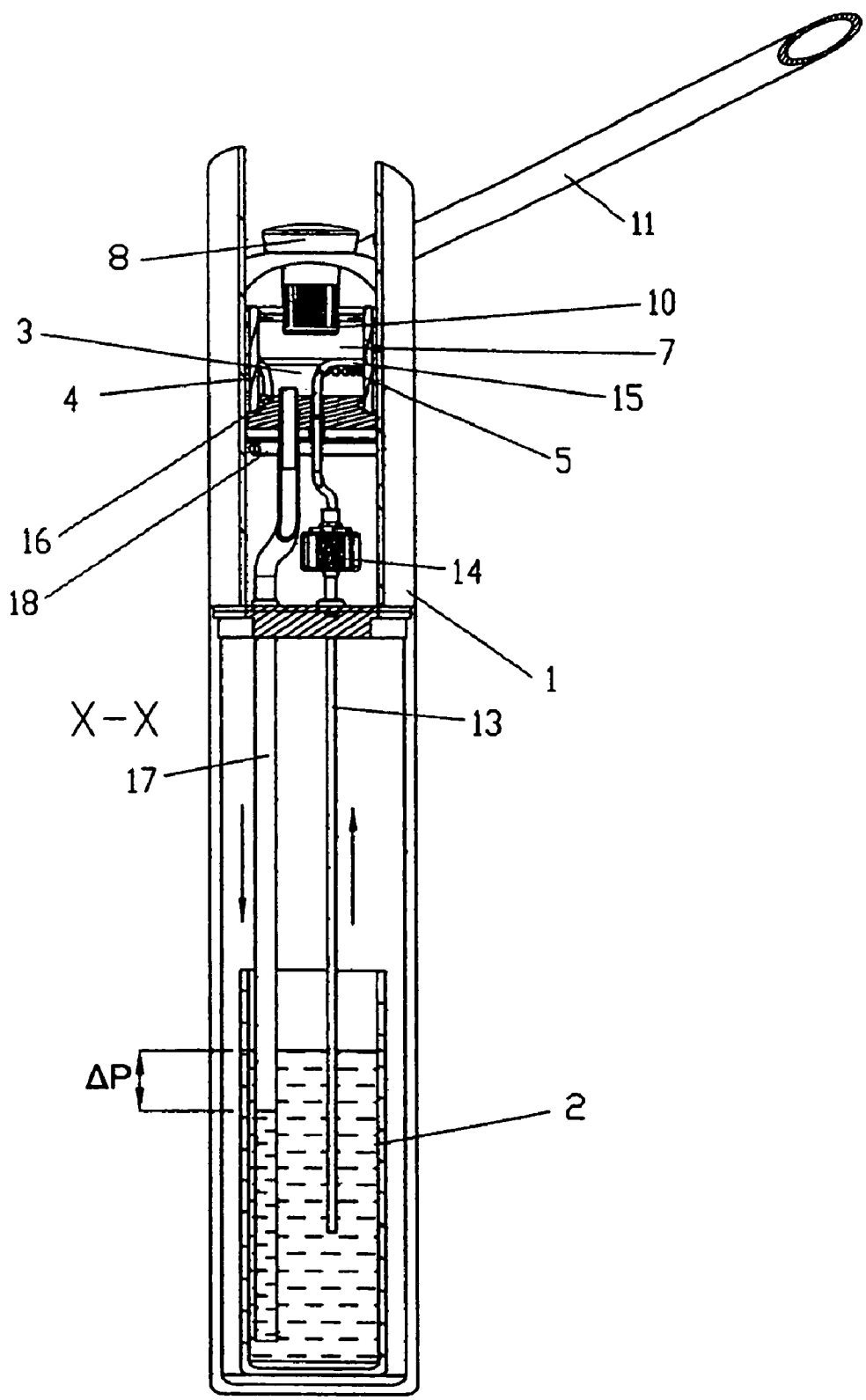
FIG. 1a shows a vertical section of a herbal steam treatment device including housing.
Figure 1B:
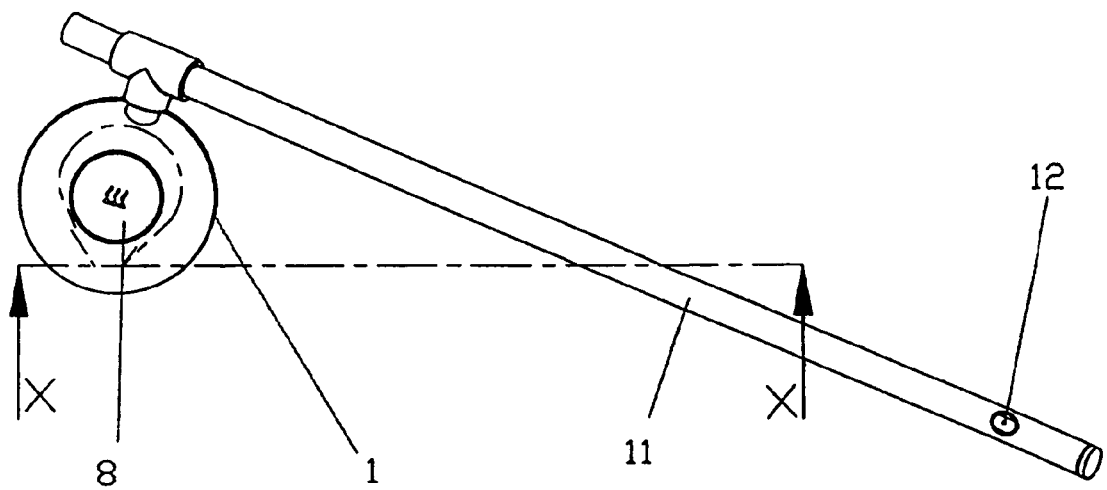

With reference to FIG. 1, a herbal steam treatment device has a cylindrical housing 1, the bottom of which may act as a stand. The surface of the presented vertical section corresponds to the line X—X in the top view of FIG. 1b.

In the lower part of the housing 1 a reservoir 2 may be arranged to hold cold water. The boiling chamber 3 may be in the head part of the steam treatment device and may take the form of a stepped cylinder. The boiling chamber 3 may be closed above. In the upper section of the boiling chamber's free side wall 4, openings 5 may be defined and may be adjacent to each other to provide a steam outlet.

Adjacent to the boiling chamber 3, a collecting chamber 6 is provided that may concentrically surround the upper part of the boiling chamber 3. From the collecting chamber 6 a short vertical channel leads to the lower part of the boiling chamber 3.

Above the boiling chamber 3 and the collecting chamber 6 a round steam space 7 may be defined or constructed. The steam space 7 may be closed above and pressure-sealed by a removable lid 8. In the upper part of the steam space 7 there may be a herb pot 10 that holds vegetable herbs. A steam pipe 11 may be connected at the side of the steam space 7. The steam which is created in the boiling chamber 3 and enriched with essential oils in the steam space 7 may flow through an outlet 12 at the end of the steam pipe 11 to the outside (see FIG. 1b).

The water stored in the reservoir 2 may flow through an inflow pipe 13 into the boiling chamber 3. An electrical pump 14 may be arranged along the inflow pipe 13 to pump the water. The upper part of the inflow pipe 13 may run in a curve 15 around the boiling chamber 3. The curve 15 may run horizontally nearby the openings 5 that provide a steam outlet from the boiling chamber 3. The inflow pipe 13 may then run vertically downwards to the lower part of the boiling chamber 3.

In the collecting chamber 6 an overflow 16 may be arranged that leads to a backflow pipe 17. The backflow pipe ends in the reservoir 2, for example, slightly above the bottom of the reservoir 2.

Under the bottom of the boiling chamber 3 an electrical heating plate 18 may be placed.

Before starting the steam treatment device the lid 8 may be unscrewed and fresh tap water may be poured in. The water is first collected in the collecting chamber 6 and then flows through the overflow 16 and the connected backflow pipe 17 downwards to the reservoir 2. After adding water, the lid 8 may again be locked.

After the turn-on, the pump 14 conveys cold water from the reservoir 2 through the inflow pipe 13 into the boiling chamber 3. The water level in the boiling chamber 3 and in the collecting chamber 6 which communicates with the boiling chamber 3 may be limited by the overflow 16. Surplus water flows automatically through the backflow pipe 17 back to the reservoir 2.

When the heating plate is switched on, the relatively small water quantity in the boiling chamber 3 will be heated within one to two minutes until boiling temperature is reached. The created steam may escape through the openings 5 of the boiling chamber 3. In the steam space 7 the steam then contacts the herbs or the plant extracts in the herb pot 10. In this way, the steam may be enriched with essential oils and may then flow through the outlet 12 of the steam pipe 11 to the outside.

Through the overflow 16 and the backflow pipe 17 the steam space 7 is in pressurized connection with the reservoir 2. There is a balance between the steam pressure in the backflow pipe 17 and the air pressure which has an effect on the water surface in the reservoir 2 and the head of water. The differential pressure $\Delta P$ may force the water level in the backflow pipe 17 to be lower than the water level in the reservoir 2. If the steam in the steam space 7 increases to a certain point, the water level in the backflow pipe 17 will sink until it is under the outlet. The steam can then be balanced between the steam space 7 and the reservoir 2. The fluid connection between the steam space 7 and the reservoir 2 over the backflow pipe may thereby act as a safety valve.

Figure 2A:
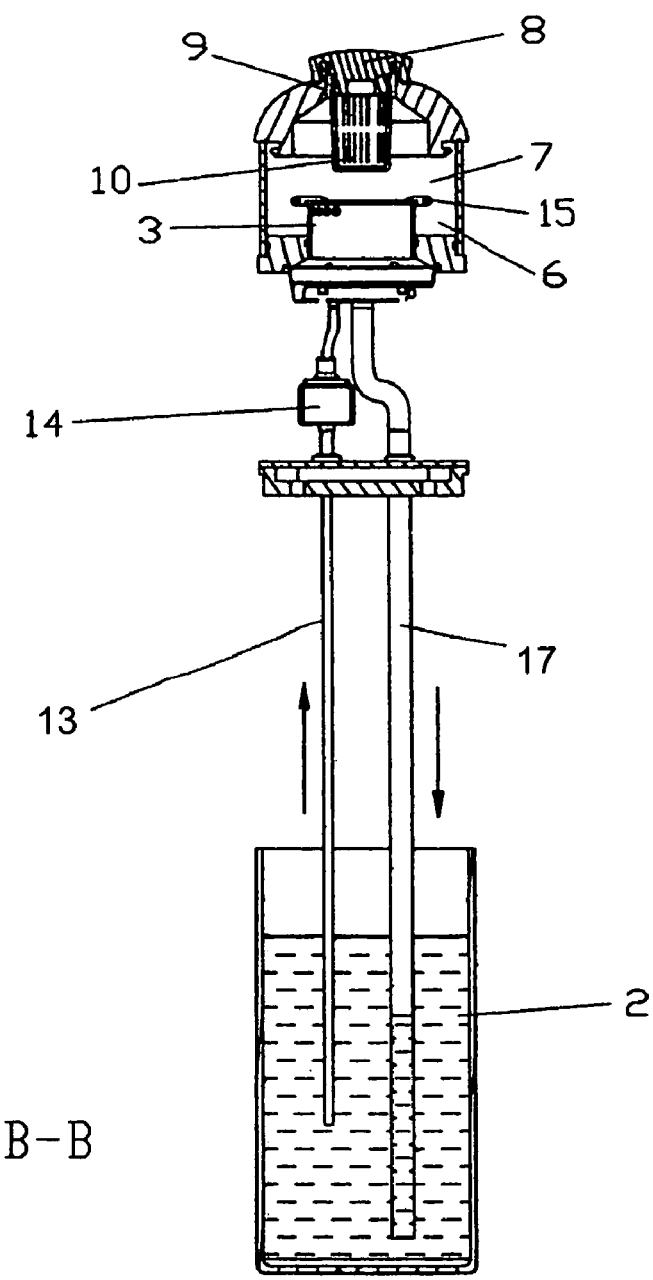
FIG. 2a illustrates a vertical section of a herbal steam treatment device without the housing.
Figure 2B:
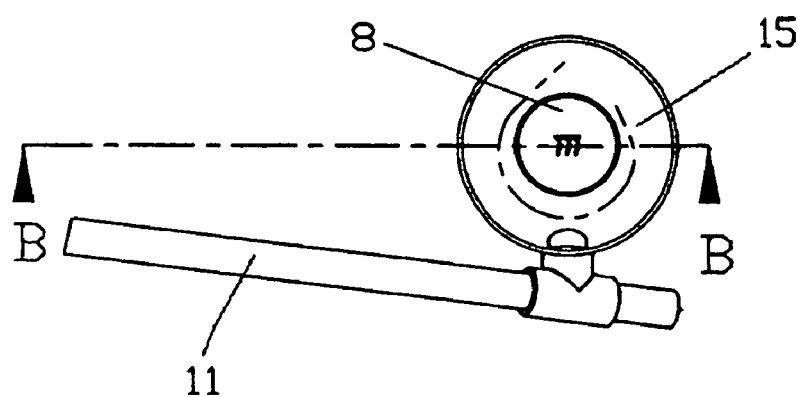

In FIG. 2a the housing and the steam pipe is omitted. The section plane B—B on FIG. 2b is through the midpoint of the cylindrical construction.

The boiling chamber 3 which may be formed cylindrically can be seen in FIG. 2a. The steam which is created in the boiling chamber 3 may escape through the openings 5 in the side wall 4. Upwards the boiling chamber 3 may be closed completely.

A herb stub 9 with the herb pot 10 inside may be located centrally over the boiling chamber 3. However, condensate with essential oils does not drop into the boiling chamber 3 but is collected in the collecting chamber 6 which surrounds the upper part of boiling chamber 3 concentrically. That way the concentration of plant extracts or essential oils in the boiling chamber 3 is kept small and there is little resulting foam.

Figure 3A:
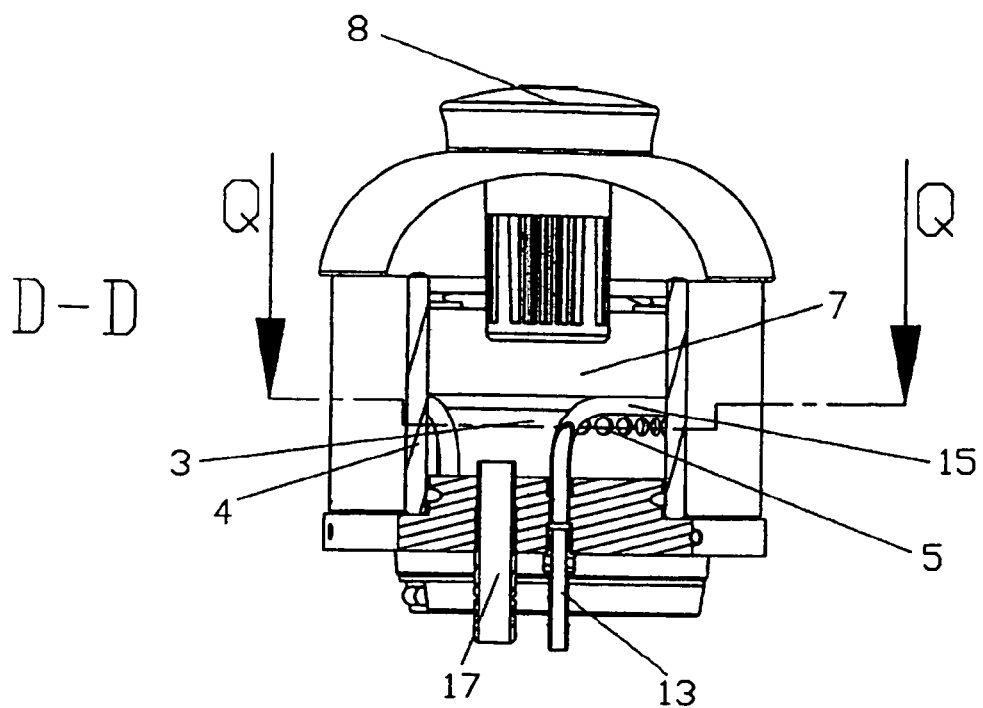
Figure 3B:
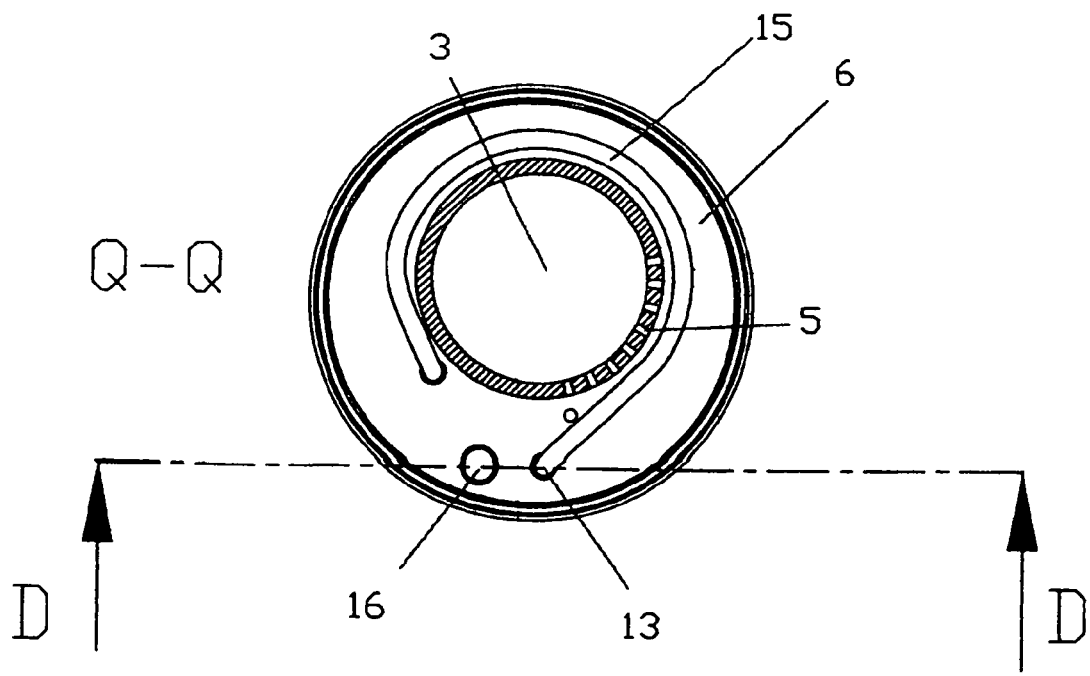
Figure 4A:
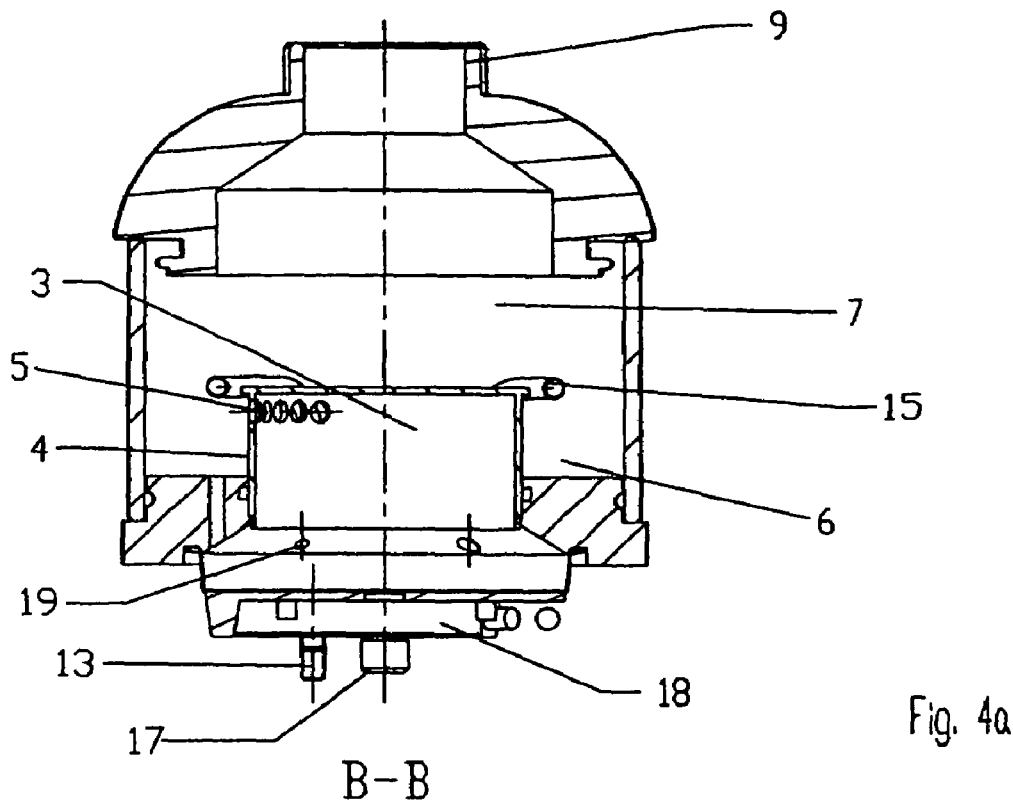
Figure 4B:
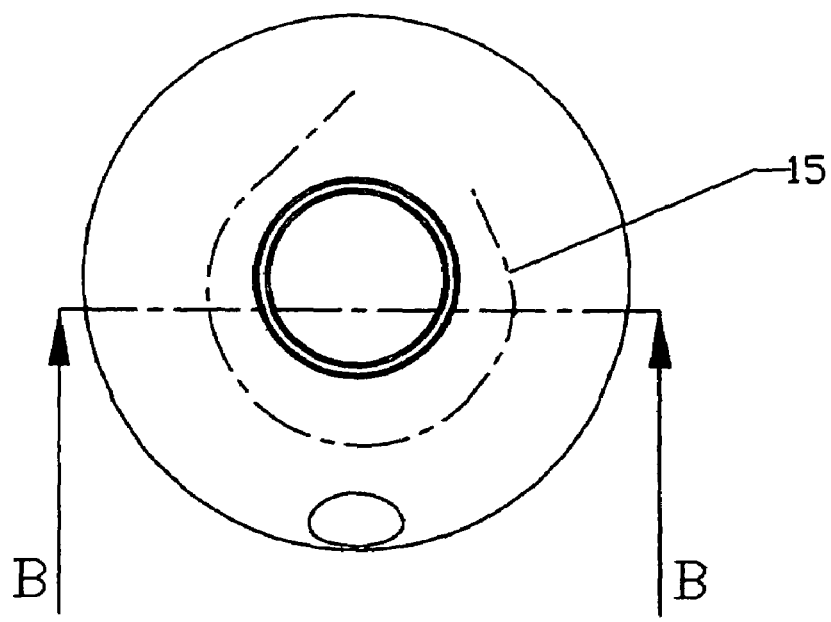

The detail views of FIG. 3a and FIG. 3b as well as FIG. 4a and FIG. 4b show how the inflow pipe 13 may surround the cylindrical boiling chamber 3 in a horizontal curve 15. The curve 15 may be located near and above the openings 5 in the side wall 4 of the boiling chamber 3. A small quantity of cold water flows through the inflow pipe 13 and the curve 15 into the boiling chamber 3. The hot steam which escapes from the openings 5 contacts the curve 15 of the inflow pipe 13. The water flowing through the curve 15 may thereby be pre-heated. In addition, any foam that escapes through the openings 5 also contacts the relatively cold curve 15 of the inflow pipe 13. The foam bubbles may then burst against the curve 15 rather than traveling out through the outlet 12. The arrangement of the openings 5 at the side wall 4 of the boiling chamber 3 in connection with the inflow pipe 13 which may narrowly surround the boiling chamber 3 in a curve 15 is an effective foam brake. A projection of the top of the boiling chamber 3 at the side (see FIG. 4a) protects the openings 5 against dripping condensate. Through the holes 19 the boiling chamber 3 may be in fluid connection with the collecting chamber 6 so that there may be the same water level in the boiling chamber 3 and the collecting chamber 6.

Figure 5:
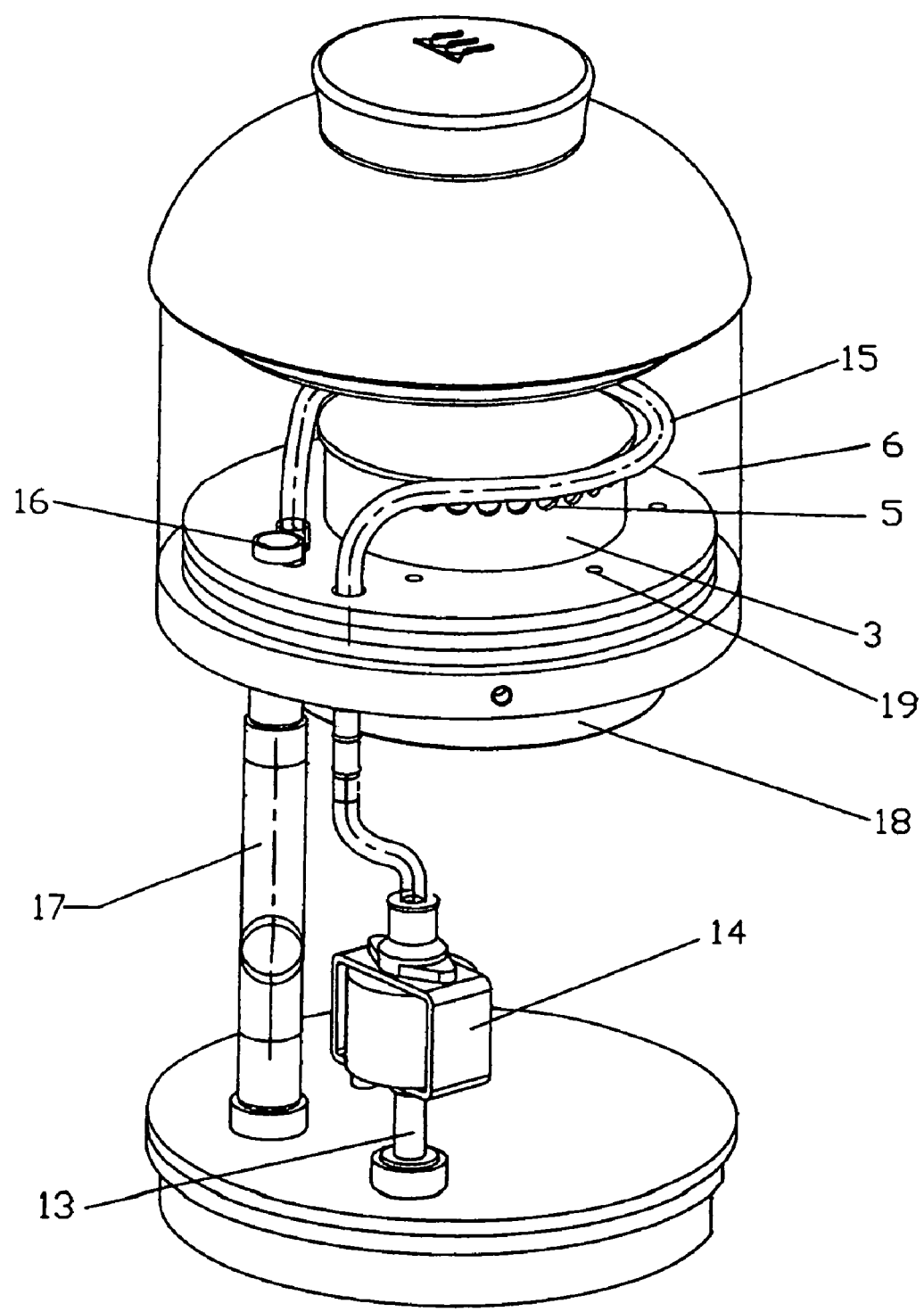

The perspective of FIG. 5 shows the cylindrical boiling chamber 3 with the openings 5 for the steam outlet and the conduit of the inflow pipe 13 in a curve 15 concentrically around the upper part of the boiling chamber 3 before it flows into the lower part of the boiling chamber 3. The openings 5 for the steam outlet may be slightly below the curve 15. The electrical pump 14 conveys the water through the inflow pipe 13. The overflow 16 passes through the lower part of the boiling chamber 3 and goes down to the backflow pipe 17. The holes 19 create a fluid connection between boiling chamber 3 and the collecting chamber 6.

It is therefore intended that the foregoing detailed description be regarded as illustrative rather than limiting, and that it be understood that it is the following claims, including all equivalents, that are intended to define the spirit and scope of this invention.

The invention claimed is:

1. A steam treatment device comprising:
 a heated boiling chamber for creating steam;
 a collecting chamber which communicates with the boiling chamber;
 a steam space in connection with the boiling chamber;
 an inflow pipe through which cold water from a reservoir passes into the boiling chamber;
 a backflow pipe through which surplus water flows from the collecting chamber to the reservoir;
 a herb pot arranged in the steam space for enriching the steam with essential oils; and
 a steam pipe connected with the steam space and comprising an outlet for the herbal steam.

2. The steam treatment device of claim 1, where the reservoir is disposed below the boiling chamber and the collecting chamber.

3. The steam treatment device of claim 1, further comprising an inflow pipe pump.

4. The steam treatment device according to claim 1, further comprising an overflow disposed in the collecting chamber that flows into the backflow pipe and that limits the water level in the boiling chamber.

5. The steam treatment device according to claim 1, where the backflow pipe ends near the bottom of the reservoir.

6. The steam treatment device according to claim 1, where:
 the boiling chamber is closed above and defines steam openings;
 the collecting chamber is adjacent to the boiling chamber; and
 the steam space is disposed above the boiling chamber and the collecting chamber so that condensate drips into the collecting chamber.

7. The steam treatment device according to claim 1, where:
 the boiling chamber is cylindrical and includes a side wall, and defines steam openings in an upper part of the side wall; and
 the collecting chamber concentrically surrounds at least an upper part of the boiling chamber.

8. The steam treatment device of claim 6, where the inflow pipe passes through the steam space near the steam openings in the boiling chamber.

9. The steam treatment device of claim 8, where the inflow pipe curves through the steam space near the steam openings in the boiling chamber.

10. The steam treatment device of claim 6, where:
 the steam space comprises a removable pressure-sealed lid; and
 further comprising a herb stub and a herb pot below the lid.

11. A steam treatment device comprising:
 a reservoir;
 a boiling chamber defining a steam outlet and in which water boils to form steam;
 a collection chamber in communication with the boiling chamber; and
 an inflow pipe coupling the reservoir to the boiling chamber, a portion of the inflow pipe forming a foam barrier located outside the boiling chamber and above and adjacent the steam outlet to burst bubbles exiting the steam outlet.

12. The steam treatment device of claim 11, further comprising an outflow pipe leading from the collection chamber to the reservoir.

13. The steam treatment device of claim 11, where the boiling chamber comprises a side wall, and where the steam outlet comprises a plurality of openings through the side wall.

14. The steam treatment device of claim 11, further comprising a herb pot above the boiling chamber.

15. The steam treatment device of claim 11, further comprising an inflow pipe pump.

16. The steam treatment device of claim 11, where the portion of the inflow pipe runs in a curve adjacent to the steam outlet.

17. The steam treatment device of claim 11, where the boiling chamber is concentric with the collection chamber.

18. A head for a steam treatment device, the head comprising:
 a boiling chamber defining a steam outlet and in which water boils to form steam;
 a collection chamber in communication with the boiling chamber;

a steam space in communication with the boiling chamber; and an inflow pipe section coupled to the boiling chamber, a portion of the inflow pipe section comprising a foam barrier located outside the boiling chamber and above and adjacent the steam outlet to burst bubbles exiting the steam outlet.

19. The head of claim 18, where the boiling chamber is concentric with the collection chamber.

20. The head of claim 18, where the boiling chamber comprises a side wall, and where the steam outlet comprises a plurality of openings through the side wall.

21. The head of claim 18, where the inflow pipe section curves at least partially around the boiling chamber.

22. The head of claim 18, further comprising a herb pot adjacent the boiling chamber.

23. The head of claim 18, further comprising a projection on the boiling chamber above the steam outlet.

24. The head of claim 18, further comprising a steam space adjacent the boiling chamber and a removable lid over the steam space.

* * * * *